United States Patent [19]

Huitema

[11] Patent Number: 5,339,723
[45] Date of Patent: Aug. 23, 1994

[54] PRESSURIZED FLUID ACTUATION SYSTEM FOR AMPLIFYING OPERATOR INPUT FORCE IN A SURGICAL INSTRUMENT

[75] Inventor: Thomas W. Huitema, Cincinnati, Ohio

[73] Assignee: Ethicon, Inc., Cincinnati, Ohio

[21] Appl. No.: 129,649

[22] Filed: Sep. 30, 1993

[51] Int. Cl.$^5$ .................. F15B 13/16; A61B 17/28
[52] U.S. Cl. ........................... 91/388; 91/403; 91/410; 91/428; 606/206
[58] Field of Search ............ 91/428, 358, 359, 388, 91/384, 385, 389, 403, 410, 465, 461; 606/131, 133, 205, 206, 207, 208, 209, 211, 51, 52

[56] References Cited

U.S. PATENT DOCUMENTS

| | | | |
|---|---|---|---|
| 3,171,329 | 3/1965 | Rasmussen | 91/388 |
| 3,628,421 | 12/1971 | George | 91/388 X |
| 4,485,817 | 12/1984 | Swiggett . | |
| 4,488,523 | 12/1984 | Shichman . | |
| 4,637,474 | 1/1987 | Leonard | 91/388 X |
| 4,721,099 | 1/1988 | Chikama . | |
| 4,815,450 | 3/1989 | Patel . | |
| 4,832,473 | 5/1989 | Ueda . | |
| 4,890,602 | 1/1990 | Hake . | |
| 4,893,613 | 1/1990 | Hake . | |
| 5,080,000 | 1/1992 | Bubic . | |
| 5,147,378 | 9/1992 | Markham | 606/206 |
| 5,179,934 | 1/1993 | Nagayoshi et al. . | |
| 5,250,074 | 10/1993 | Wilk et al. | 606/207 |
| 5,271,313 | 12/1993 | Lindegren | 91/403 X |

OTHER PUBLICATIONS

U.S. patent application Ser. No. 08/130,068 entitled "Articulable Socket Joint Assembly For An Endoscopic Instrument And Surgical Fastener Track Therefor". F.D: Sep. 30, 1993.

U.S. patent application Ser. No. 08/129,976 entitled "Pressurized Fluid Actuation System With Variable Force And Stroke Output For Use In A Surgical Instrument". F.D.: Sep. 30, 1993.

U.S. patent application Ser. No. 08/130,065. F.D: Sep. 30, 1993.

*Primary Examiner*—Edward K. Look
*Assistant Examiner*—Hoang Nguyen
*Attorney, Agent, or Firm*—Dressler, Goldsmith, Shore & Milnamow, Ltd.

[57] ABSTRACT

A pressurized fluid actuation system as provided for a surgical instrument. The system includes a double-acting fluid pressure actuator with an extension chamber and a retraction chamber separated by a piston for engaging a component of the instrument. An operating lever is pivotally mounted to the piston. The operating lever is also pivotally connected to a servo valve that has a valve spool. The valve is connected to a source of pressurized fluid and has first and second return ports for venting the fluid. The actuator extension and retraction chambers are connected with the valve for each communicating with the pressurized fluid source and with one of the return ports in response to the position of the valve spool. The system includes a feedback line communicating between the extension chamber and the valve to apply a force to the valve spool in one direction when the extension chamber is pressurized. The system also includes a sensing line communicating between the retraction chamber and the valve to apply a force to the valve spool in the opposite direction when the retraction chamber is pressurized.

14 Claims, 6 Drawing Sheets

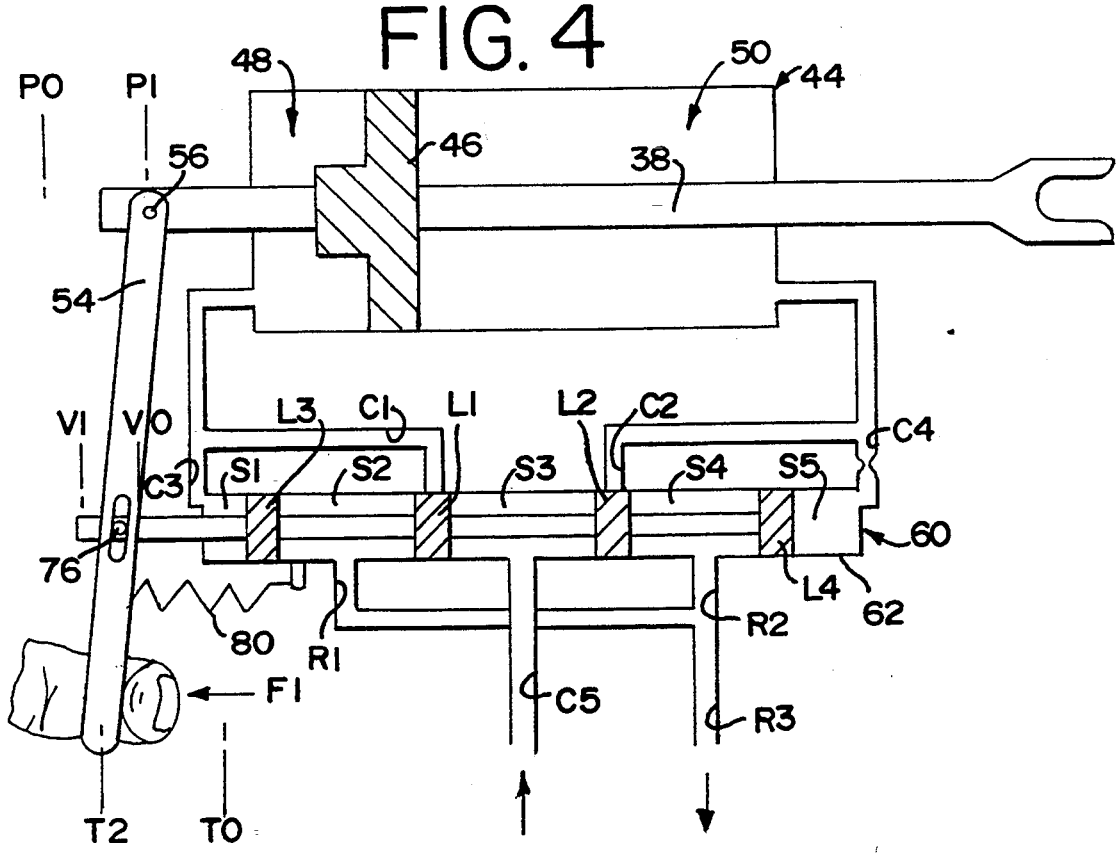

PRESSURIZED FLUID ACTUATION SYSTEM FOR AMPLIFYING OPERATOR INPUT FORCE IN A SURGICAL INSTRUMENT

TECHNICAL FIELD

This invention relates generally to an actuation system for surgical instruments, including instruments used in endoscopic procedures as well as in open surgery procedures. This system is particularly suitable for incorporation in a ligating clip applier or stapler wherein it is desirable to provide tactile feedback, force amplification, controlled movement of jaws or other components, and smooth operation.

BACKGROUND OF THE INVENTION AND TECHNICAL PROBLEMS POSED BY THE PRIOR ART

A variety of designs have been commercialized or proposed for actuators in instruments that operate a tissue-engaging end effector (e.g., a pair of cooperating jaws in which one or both jaws pivot or otherwise move between open and closed positions). Examples of such instruments include tissue graspers, tissue clamps, needle graspers, tissue cutters, linear staplers, ligating clip appliers, and the like.

In some surgical applications, it is necessary or advantageous to apply relatively high squeezing forces. Thus, it would be desirable to provide an improved actuation system that can provide an amplification effect for increasing the force applied by the jaw (or other end effector) compared to the operator input force. It would also be beneficial if the system could accommodate designs wherein the reaction force or load is sensed by the operator. Such tactile feedback would be advantageous in delicate operations.

Some instruments, such as some clip appliers, include spring-biased or spring-actuated internal components which can create significant impact reactions within the instrument. This can produce undesirable noise and movement. Accordingly, it would be beneficial to provide an improved actuation system for moving a tissue end effector (e.g., jaws) in a controlled and quiet manner.

It would further be desirable to provide an improved actuation system having a reduced number of components, such as mechanical linkages, rachet mechanisms, and the like, so as to simplify fabrication and so as to minimize friction losses.

Finally, it would also be beneficial if such an improved system could be provided with sufficient capacity and strength to accommodate relatively high loads during operation of the instrument.

The present invention provides an improved actuation system which can be used to operate a surgical instrument and which can accommodate designs having the above-discussed benefits and features.

SUMMARY OF THE INVENTION

According to the principles of the present invention, a pressurized fluid actuation system is provided for moving an endoscopic or open surgical procedure instrument component. The system is particularly suitable for use in instruments such as ligating clip appliers wherein it is desirable to have tactile feedback, force amplification, controlled movement of the end effector, and smooth operation.

The system includes a double-acting fluid pressure actuator defining an extension chamber and a retraction chamber separated by a piston for engaging the component. An operating lever is pivotally mounted to the piston.

A servo valve is provided with a valve spool that is pivotally connected on one end to the lever. The valve is connected to a source of pressurized fluid and has first and second return ports for venting the fluid.

The actuator extension and retraction chambers are connected with the valve for each communicating with the pressurized fluid source and with one of the return ports so that flow is controlled in response to the position of the valve spool.

The system includes a feedback line communicating between the extension chamber and the valve to apply force to said valve spool in one direction in response to pressurization of the extension chamber. This system also includes a sensing line communicating between the retraction chamber and the valve to apply force to said valve spool in the opposite direction in response to pressurization of the retraction chamber. This system provides both position control and load sensing at the operator lever.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIGS. 2, 3, and 4 are schematic, hydraulic circuit diagrams of the fluid actuation system, or portions thereof, shown in FIG. 1, and these figures illustrate the various conditions of the system operation;

FIG. 5 is a greatly enlarged, fragmentary, simplified, cross-sectional view of a portion of the instrument of a second embodiment of the fluid actuation system; and FIG. 6 is a greatly enlarged, fragmentary, simplified, cross-sectional view of a portion of the instrument of a third embodiment of the fluid actuation system.

DESCRIPTION OF THE PREFERRED EMBODIMENTS

One aspect of the present invention relates to a fluid actuation system which can be employed to operate surgical instruments and which can be incorporated in a variety of designs providing unique operational characteristics and capabilities.

The actuation system can be employed in instruments for operating devices to effect a variety of functions with respect to the surgical site. Such functions can include, but are not limited to, grasping, clamping, and applying staples or ligating clips. The actuation system is especially suitable for use in a ligating clip applier instrument.

Various embodiments of the actuation system can be provided in an instrument with sufficient interior space to accommodate internal passages and components (e.g., sensor lines and components, conduits, fastener actuation systems, etc.).

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the embodiments of the actuation system of this invention are described in various operating positions, and terms such as upper, lower, horizontal, etc., are used with reference to these positions. It will be understood, however, that the system components of this invention may be manufactured, stored, transported, used, and sold in an orientation other than the positions described.

Some of the actuation system mechanical elements illustrated in the figures are known and will be recognized by one skilled in the art. The detailed descriptions of such elements are not necessary to an understanding of the invention, and accordingly, are herein presented only to the degree necessary to facilitate an understanding of the novel features of the present invention.

The actuation system incorporating the present invention can be used in instruments that have certain conventional components the details of which, although not fully illustrated or described, will be apparent to those having skill in the art and an understanding of the necessary functions of such instrument components.

Figure 1:
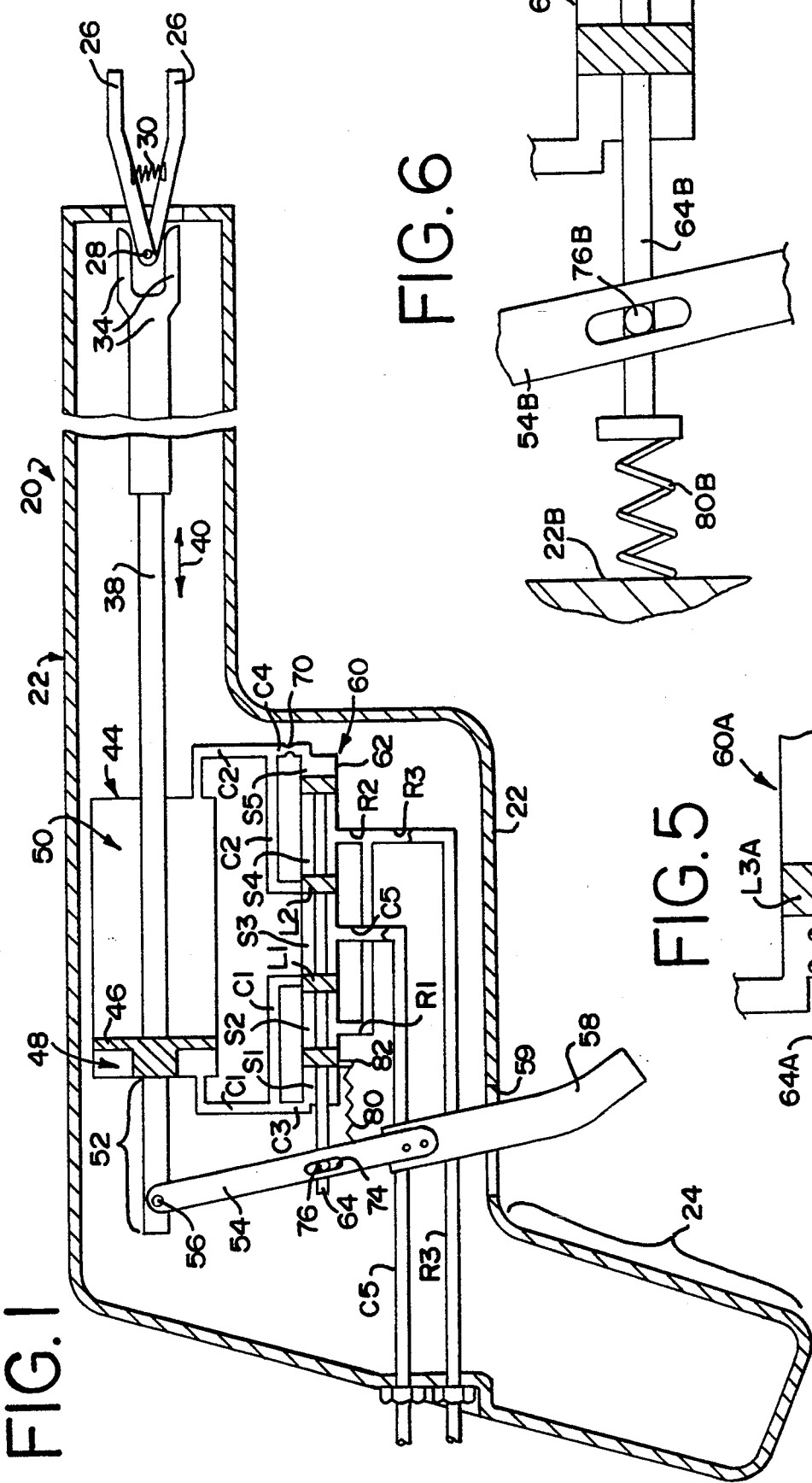
FIG. 1 is a simplified, partially diagrammatic, cross-sectional view of a surgical instrument incorporating a first embodiment of the fluid actuation system of the present invention which is schematically illustrated with a hydraulic circuit diagram.
Figure 2:
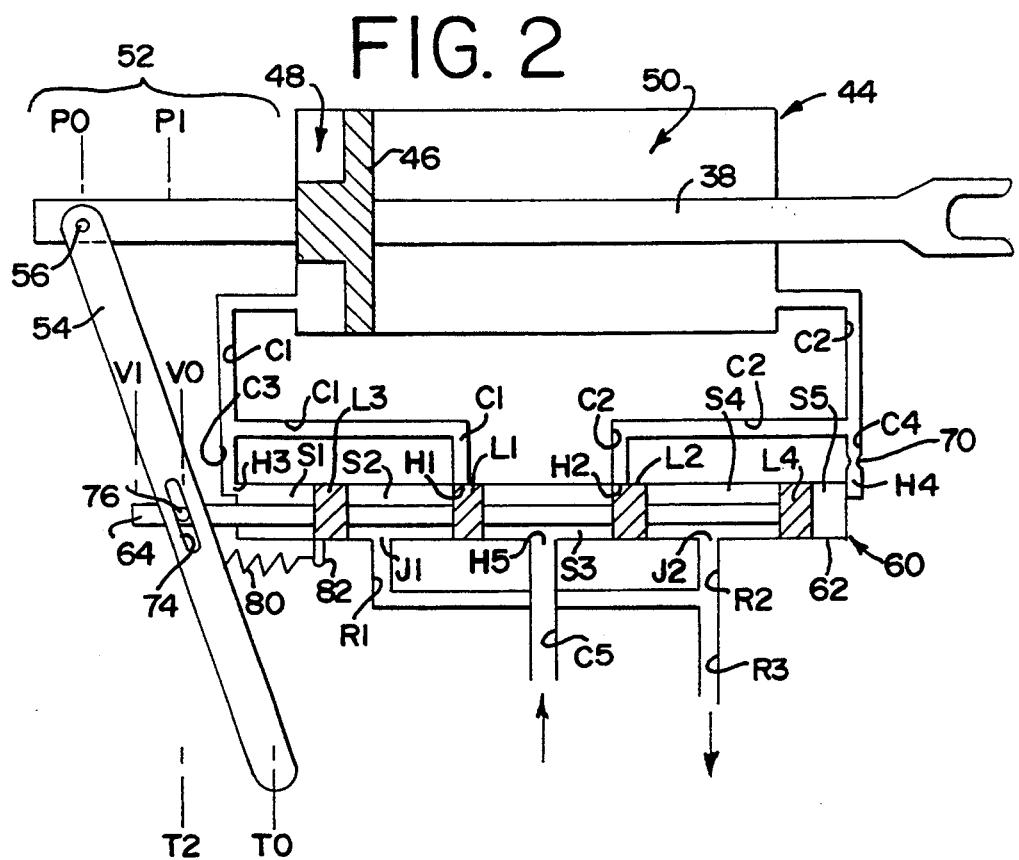

FIGS. 1, 2, 2A, 3, 3A, 3B, 4, 4A, and 4B schematically illustrate some basic features of a first embodiment of the actuation system of the present invention. The system is adapted to be incorporated in an open surgery or endoscopic instrument 20, and part of the instrument may typically include a support housing 22 (FIG. 2). The instrument 20 preferably has a pistol grip handle 24 which is grasped by the surgeon. In an endoscopic instrument, a proximal part of the housing 22 remains outside of the patient while the rest of the instrument is inserted through the trocar cannula (not illustrated) and into the body cavity.

The instrument 20 is a jaw assembly comprising a pair of jaws 26 which are pivotally mounted to the housing on a pin 28. The jaws 26 are normally biased outwardly to an open position by a spring 30. The jaws 26 are forced closer together, to a closed position, when engaged by a forwardly moving cam channel 34 at the end of a rod 38.

The assembly of the jaws 26 and the cam channel 34 is diagrammatically illustrated for simplicity in FIG. 1, and the specific design of such components forms no part of the present invention. Such a jaw assembly may be employed for grasping tissue or for applying a ligating clip (not illustrated) to tissue, such as to a blood vessel. Depending upon the actual structure of the jaw assembly, a plurality of ligating clips or other fasteners could be applied simultaneously or seriatim.

Instead of a jaw assembly, the distal end of the instrument 20 could be provided with other components or end effectors such as tissue cutters, staplers, and the like. Indeed, the end effector could include a needle or probe-like member for longitudinal movement in response to movement of the rod 38 in either of the opposite directions illustrated by the double headed arrow 40.

The rod 38 is operated by a double-acting, fluid, servo actuator or actuator 44. The rod 38 extends into the actuator housing or cylinder and is connected to a piston 46 therein. The piston 46 separates an extension chamber 48 on one side from a retraction chamber 50 on the other side. The piston rod 38 includes a rear portion 52 which projects from the piston 46 and through the housing of the actuator 44.

An operating lever 54 is pivotally mounted to the rod rear portion 52 by means of a pin 56. An extension portion or trigger 58 is mounted to the lower, distal end of the operating lever 54. The trigger 58 projects downwardly through a slot 59 defined in the instrument housing 22. The trigger 58 may be squeezed by a surgeon's finger or fingers when the surgeon holds the instrument in one hand by the handle 24.

A servo valve 60 is provided in the instrument 20 and is supplied with pressurized hydraulic fluid through a supply line C5. Low pressure hydraulic fluid is returned or vented from the valve 60 through return lines R1 and R2 which communicate with a common return line R3.

The supply line C5 and the return line R3 are adapted to be connected to a suitable, pressurized, hydraulic fluid supply system (not illustrated) which may be of any suitable conventional or special design. The detailed design and operation of such a hydraulic fluid system form no part of the present invention.

The design of the servo valve 60 and its connections with the operating lever 54 and servo actuator 44 are illustrated in an enlarged scale in FIG. 2. With reference to FIG. 2, the servo valve 60 has a body 62 defining an internal cavity in which is slidably disposed a valve spool comprising a rod 64 and four valve members or lands L1, L2, L3, and L4. The valve spool members or lands L1–L4 are longitudinally spaced-apart along the valve spool rod 64.

The valve body 62 defines a supply port H5 to which the hydraulic fluid supply line C5 is connected. The body 62 also defines a first return port J1 to which the return line R1 is connected. The valve body 62 has a second return port J2 to which the return line R2 is connected.

The valve 60 is connected with the servo actuator 44. A line C1 extends from the actuator extension chamber 48 to an extension port H1 defined by the valve body 62. A line C2 establishes fluid communication between the actuator retraction chamber 50 and a retraction port H2 defined by the valve body 62.

The valve body 62 defines a feedback port H3 at the left-hand end of the valve body, and the feedback port H3 is connected to a feedback line C3 which is in turn connected with the line C1 for communicating at the actuator extension chamber 48.

The right-hand end of the valve body 62 defines a sensing port H4 which is connected to a sensing line C4. The sensing line C4 is connected to the line C2 for communicating with the actuator retraction chamber 50. The sensing line C4 also preferably includes a flow restrictor 70.

The valve member L1 is located on the valve spool rod 64 so that it is generally to the left of the supply port H5 throughout its range of movement. Similarly, the valve member L2 is located on the valve spool rod 64 so that it is generally on the right-hand side of the supply port H5 throughout its range of movement.

The valve member L3 is located on the valve spool shaft 64 so that it is between the feedback port H3 and the first return port J1 throughout the range of movement of the valve member L3. A feedback chamber S1 is defined adjacent the port H3. Similarly, at the other end of the valve 60, the valve member L4 is located so that it is between the sensing port H4 and the second return port R2 throughout the range of movement of the valve member L4. A sensing chamber S5 is defined adjacent the port H4.

The lever 54 can be moved, as when the surgeon engages the trigger 58 (FIG. 1), to position the valve members L1–L4 relative to the valve body 62 ports. To this end, the operating lever 54 defines a slot 74, and the valve spool rod 64 carries a laterally projecting pin 76 which is received in the slot 74. The lever 54 is normally biased toward the valve 60 by means of a tension spring 80 that is connected at one end to a bracket 82 on the valve body and that is engaged at the other end with the lever 54.

FIG. 2 illustrates an initial, rest position in which the system is pressurized. That is, pressurized hydraulic fluid is supplied to the valve 60 through the supply line C5. In this position, the servo actuator piston 46 is located at the left-hand end of its stroke.

Figure 2A:
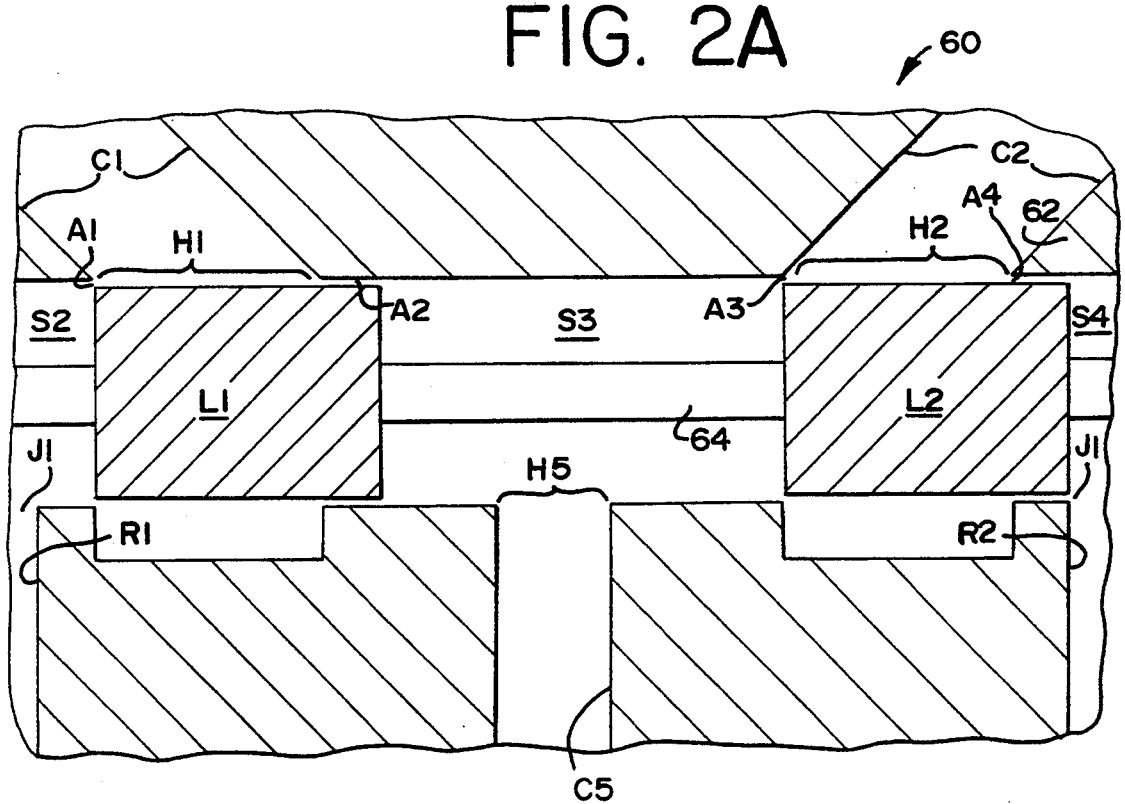
FIGS. 2A, 3A, 3B, 4A, and 4B are each simplified, partly diagrammatic, greatly enlarged, cross-sectional view of a portion of the servo valve which is only schematically illustrated in FIGS. 1, 2, 3, and 4.

FIG. 2A illustrates, on an enlarged scale, a portion of the servo valve 60 in the position that is schematically represented in FIG. 2. Typically, the valve members L1 and L2 (as well as members L3 and L4), are cylindrical, and the cavity within the valve body 62 around the valve members is also cylindrical. There is an annular clearance between the valve body 62 and each valve member. For purposes of illustration, FIGS. 2A, 3A, 3B, 4A, and 4B exaggerate the clearances relative to the size of the valve members. Each annular clearance is typically on the order of about 0.001 inch. The pressurized hydraulic fluid can flow through the annular clearances or around the valve members. Thus, with reference to FIG. 2A, the pressurized fluid between the valve members L1 and L2 can flow past the valve member L1 and past the valve member L2 from the central space between the two valve members which, in FIG. 2A, is designated generally by the reference characters S3.

The axial length of the annular space along each end of a valve member varies with, and depends upon, the axial position of the valve member in the valve body 62 relative to the adjacent extension port H1 or retraction port H2. The pressure drop developed as the fluid flows through the length of the annular clearance space varies with, and is generally proportional to, the axial length of the clearance space.

In FIG. 2A the clearance space at the left-hand end of the valve member L1 is generally designated as A1, and the length of the annular clearance at the right-hand end of the valve member L1 is generally designated as A2.

The length of the annular clearance space at the left-hand of the valve member L2 is generally designated as A3, and the length of the annular clearance space at the right-hand end of the valve member L2 is generally designated as A4.

In the position illustrated in FIG. 2A, the left-hand end of the valve member L2 is located substantially at the edge of the retraction port H2. The length of the annular clearance A3 is relatively short.

On the other hand, the length of the annular clearance A2 at the right-hand end of the valve member L1 is considerably longer. Accordingly, the hydraulic fluid flowing from the supply region $3 between the two valve members L1 and L2 into the line C1 is subjected to a significant pressure drop compared to the fluid passing through the much shorter annular clearance A3 at the valve member L2. As a result of the larger pressure drop created by the valve member L1, the pressure in the line C1 and at the actuator extension chamber 48 is considerably less than the pressure in the line C2 and at the actuator retraction chamber 50. For example, in one typical valve construction, the pressure in the actuator retraction chamber 50 might be about twice the pressure in the actuator extension chamber 48 when the valve 60 is in the position shown in FIG. 2A. This differential maintains the actuator piston 46 in the retracted position at the left-hand end of the actuator 44 as illustrated in FIG. 2.

When the actuator 44 is retracted as illustrated in FIG. 2, the rod portion 52 extending to the left of the piston 46 is located at the extreme left-hand position of its range of movement. In this position, the pin 56 connecting the rod portion 52 to the lever 54 is at an initial location P0. The pin 76 connecting the servo valve rod 64 to the lever 54 is at an initial position V0. The lower end of the lever 54 may be characterized as having an initial location T0.

In the retracted position illustrated in FIGS. 2 and 2A, the lower pressure in the actuator extension chamber 48 is also communicated through the feedback line C3 to a feedback chamber S1 defined at the left-hand end of the valve body 62. Any fluid leaking from the chamber S1 past the valve member L3 flows into an intermediate chamber $2 between the valve member L3 and the valve member L1. Such fluid flows out through the return line R1. Fluid flowing past the valve member L1 into the chamber $2 is also vented out the return line R1.

At the right-hand half of the valve 60, fluid flowing past the valve member L2 is received in the chamber S4 defined between the valve members L2 and L4. Such fluid is vented out of through the return line R2. Hydraulic fluid leaking from the chamber S5 at the right-hand end of the valve body 62 past the valve member L4 flows to an intermediate chamber S4 and then out through the return line R2.

Because the high pressure in chamber S3 acts on both the valve member L1 and L2, the high pressure forces are balanced on the facing sides of the members L1 and L2. The pressure in the right-hand end sensing chamber S5 is greater than the pressure in the left-hand end feedback chamber S1. However, the additional force provided by the tension spring 80, when added to the force provided by the hydraulic fluid and chamber S1, equals the opposing force provided by the fluid in the chamber S5.

If the valve spool rod 64 moves slightly toward the right, the increasing pressure drop through the clearance A2 would reduce the pressure in the left-hand chamber S1, and the decreasing pressure drop through the clearance A3 would increase the pressure in the right-hand chamber S5. This would tend to move the valve spool rod 64 back to the position illustrated in FIGS. 2 and 2A.

Similarly, if there was a slight movement of the valve spool rod 64 toward the left, the decreasing pressure drop through the clearance A2 would increase the pressure in the left-hand end feedback chamber S1 while the increasing pressure drop through the clearance A3 would decrease the pressure in the right-hand end sensing chamber S5. This would tend to return the valve spool back to the position illustrated in FIGS. 2 and 2A.

Figure 3:
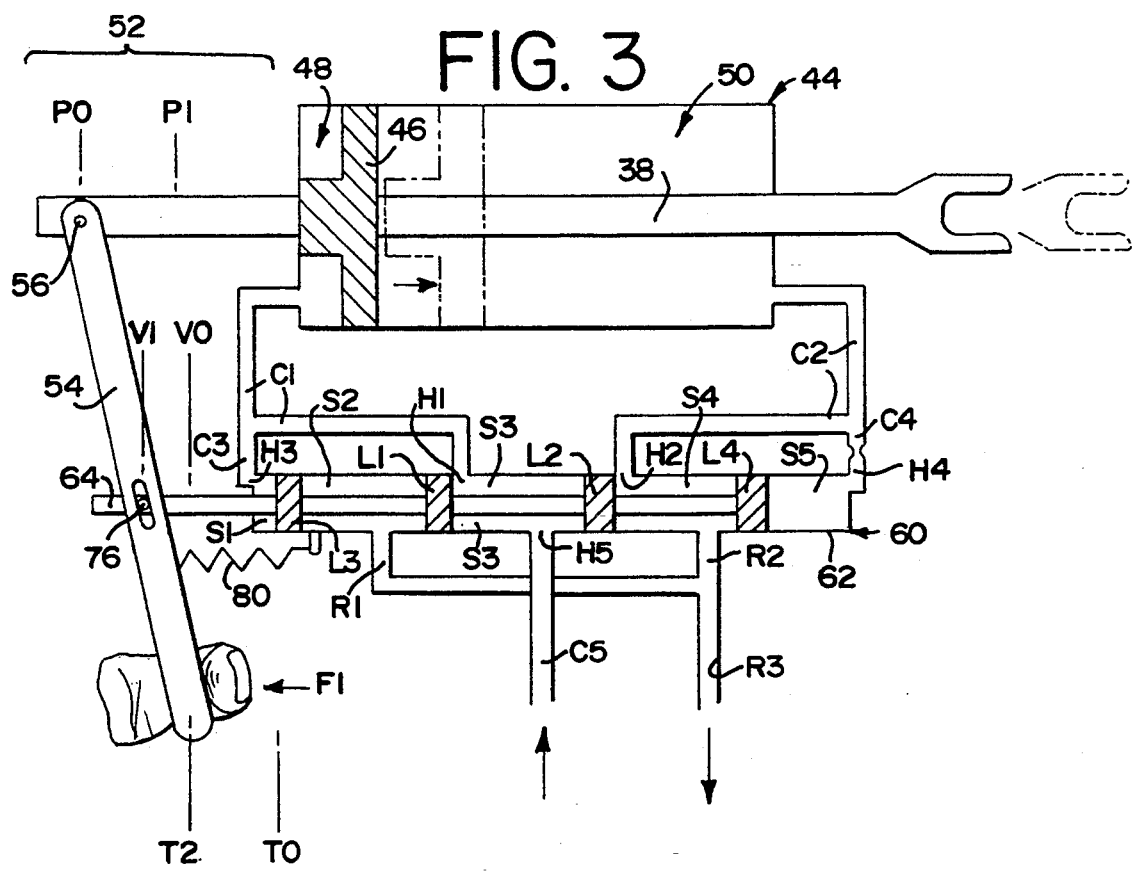
Figure 3A:
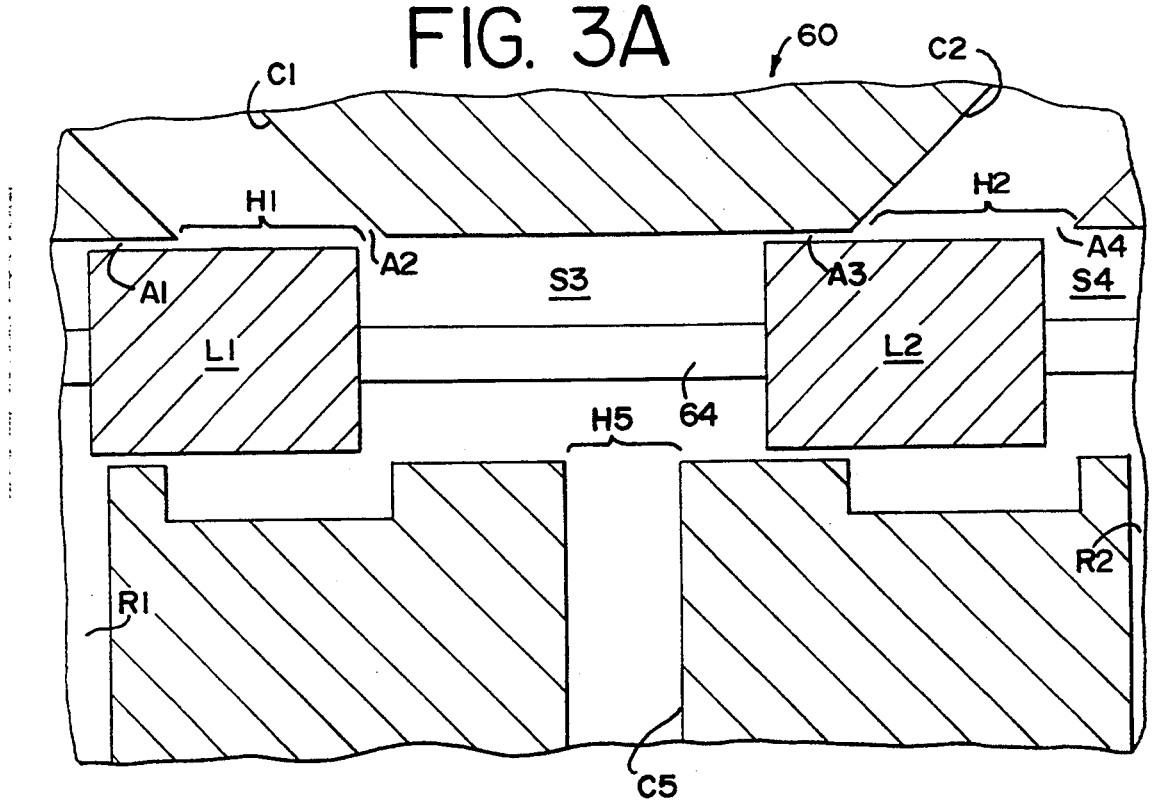

The actuation system can be initially operated by the surgeon as illustrated in FIGS. 3 and 3A. The surgeon pulls the operating lever 54 toward the left, with a force F1, from the initial position T0 to an intermediate position T2 as illustrated in FIG. 3. As the bottom of the lever 54 moves to the left, the lever pivots about the pin 56 on the actuator rod portion 52. This moves the connecting pin 76 on the valve spool rod 64 to a position V1 and pulls the valve spool toward the left so that each valve member L1, L2, L3, and L4 moves to the left within the valve body 62. As the lever 54 moves to the left, the lever also pivots in a clockwise direction about the pin 76. As the servo valve spool valve member L1 moves to the left, the line C1 and actuator extension chamber 48 become more pressurized. When the extension chamber pressure exceeds the pressure in the retraction chamber 50, the piston 46 begins to move to the right along the actuator 44 as indicated by the intermediate position shown in dashed lines in FIG. 3.

FIG. 3A illustrates, on an enlarged scale, a portion of the servo valve 60 in the position that is schematically represented in FIG. 3. The valve spool rod 64 has been moved further to the left and carries with it the valve members, including valve member L1 and valve member L2. The length of the annular clearance A3 at the valve member L2 has now increased so that the fluid encounters greater pressure drop when flowing from the central chamber S3 to the line C2. On the other hand, the flow area at the clearance A4 has become substantially greater. Under these conditions, there is moderate flow through clearance A2 and through clearance A4 to support moderate flow rates.

The servo valve 60 would be in the position generally shown in FIG. 3A if the servo actuator 44 were stroking at moderate speed under moderate load. If the servo actuator piston 46 was moved all the way to the right-hand end of the actuator 44 and prevented from further movement by the right-hand end of the housing of the actuator 44, then the pressure in the line C1 and actuator extension chamber 48 would substantially equal the supply pressure in the central chamber S3. At the same time, the pressure in the line C2 and the actuator retraction chamber 50 would substantially equal the pressure in the return line R2.

Figure 3B:
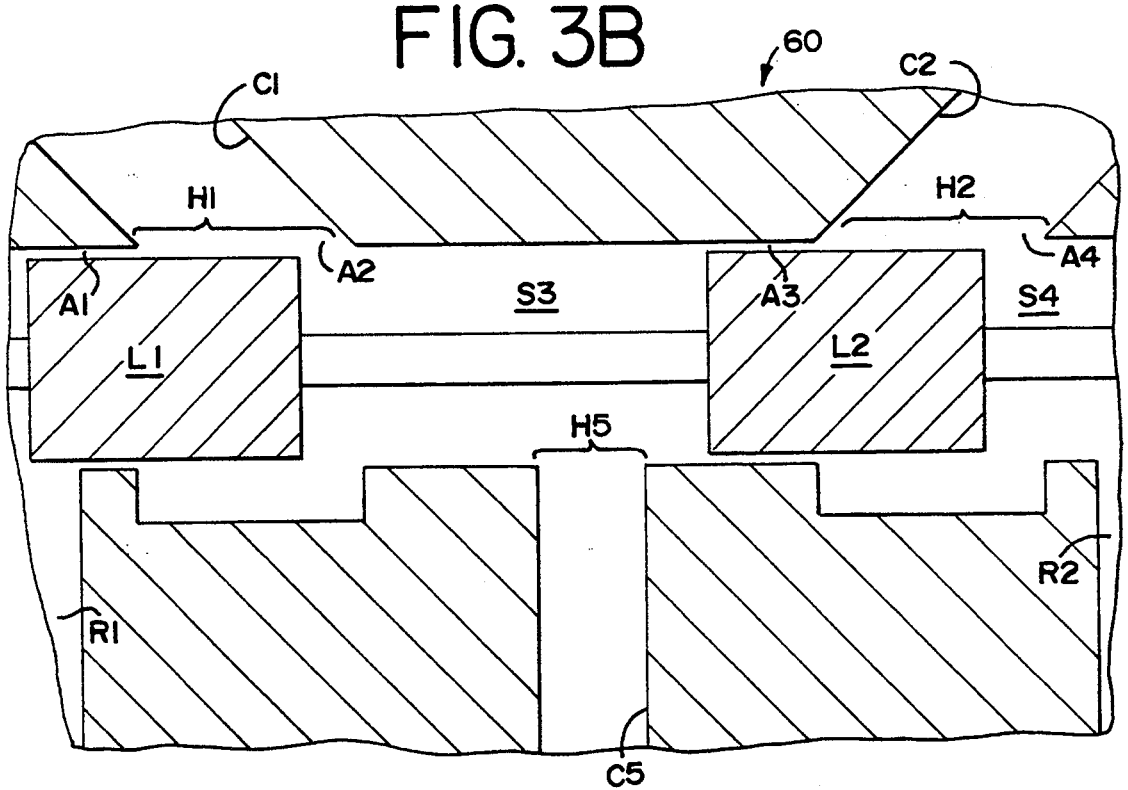

FIG. 3B illustrates the servo valve 60 shifted even further to the left. In this position, the spool valve member L1 has opened more to provide a greater inlet flow to the actuator 44, and the valve member L2 has opened to provide a greater outlet flow from the actuator 44. Specifically, the flow area or clearance A2 between the central chamber S3 and the line C1 has increased, and the flow area at clearance A4 between the line C2 and the return chamber S4 has increased. This accommodates substantial flow rates of the hydraulic fluid. Thus, the servo valve 60 can support a higher combination of servo actuator speed and load than when the valve member 60 is in the position illustrated in FIG. 3A.

FIG. 4 shows the servo valve 60 in a centered or nulled position. In this position the lever 54 has rotated about the valve spool link pin 76 such that the lever connection pin 56 on the actuator rod has moved to a position P1. The valve spool with the valve members L1–L4 has moved to the right, and the valve spool link pin 76 is located between its left-hand position V1 and the extreme right-hand, initial position P0.

This position of the servo valve 60 could result if the surgeon pulled the operating lever 54 just enough to overcome the biasing spring 80 and there was no external load on the servo actuator 44. This results in the servo actuator 44 being maintained in a rest position somewhere along its stroke.

Figure 4A:
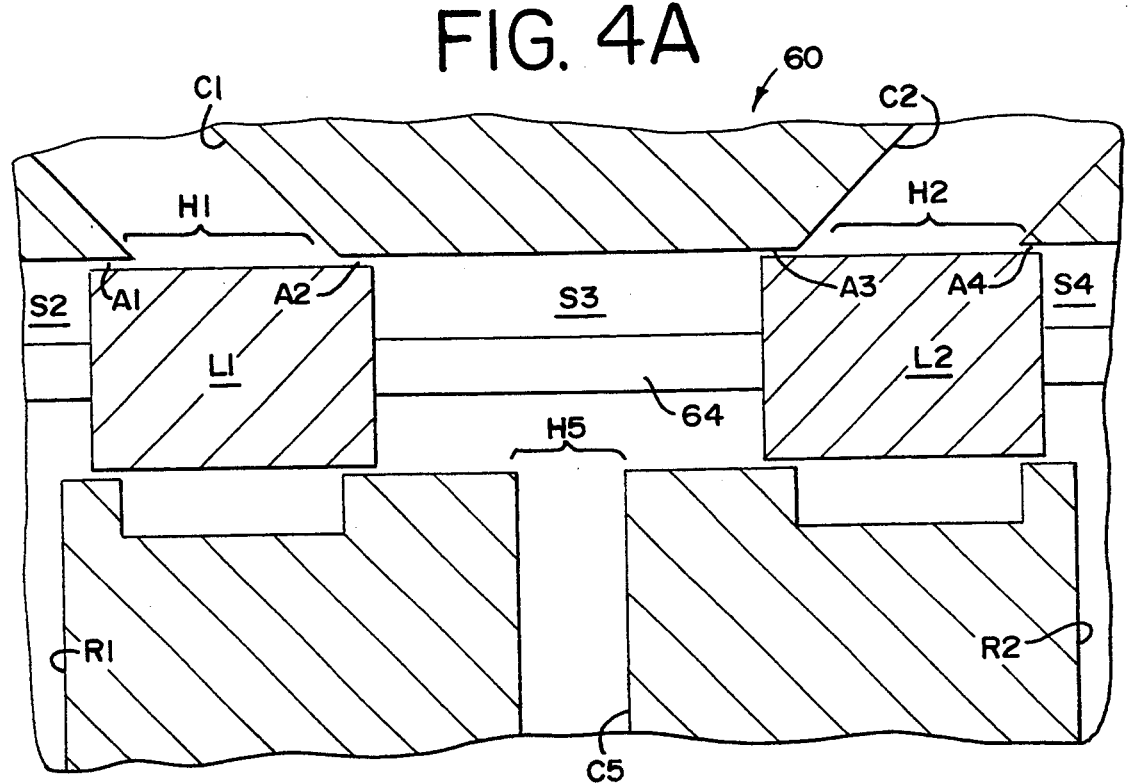

The position of the servo valve 60 in FIG. 4 is shown in an enlarged scale in FIG. 4A. The valve member L1 is generally centered at the extension port H1, and the valve member L2 is generally centered at the retraction port H2. This results in the length of the annular clearance A2 being substantially equal to the annular clearance A3. Thus, the hydraulic fluid flows from the central chamber S3 through the clearance A2 and clearance A3 with substantially equal pressure drops.

For illustrative purposes, if it is assumed that the pressure drop is one half of the supply pressure, then the pressure in the extension line C1 will be ½ of the supply pressure, and the pressure in the retraction line C2 will be ½ of the supply pressure. Thus, the actuator retraction chamber 50 will be subjected to ½ of the supply pressure and the extension chamber 48 will be subjected to ½ of the supply pressure. Similarly, the left-hand end feedback chamber S1 will be subjected to ½ of the supply pressure, and the right-hand sensing chamber S5 will be subjected to ½ half of the supply pressure S5.

Figure 4B:
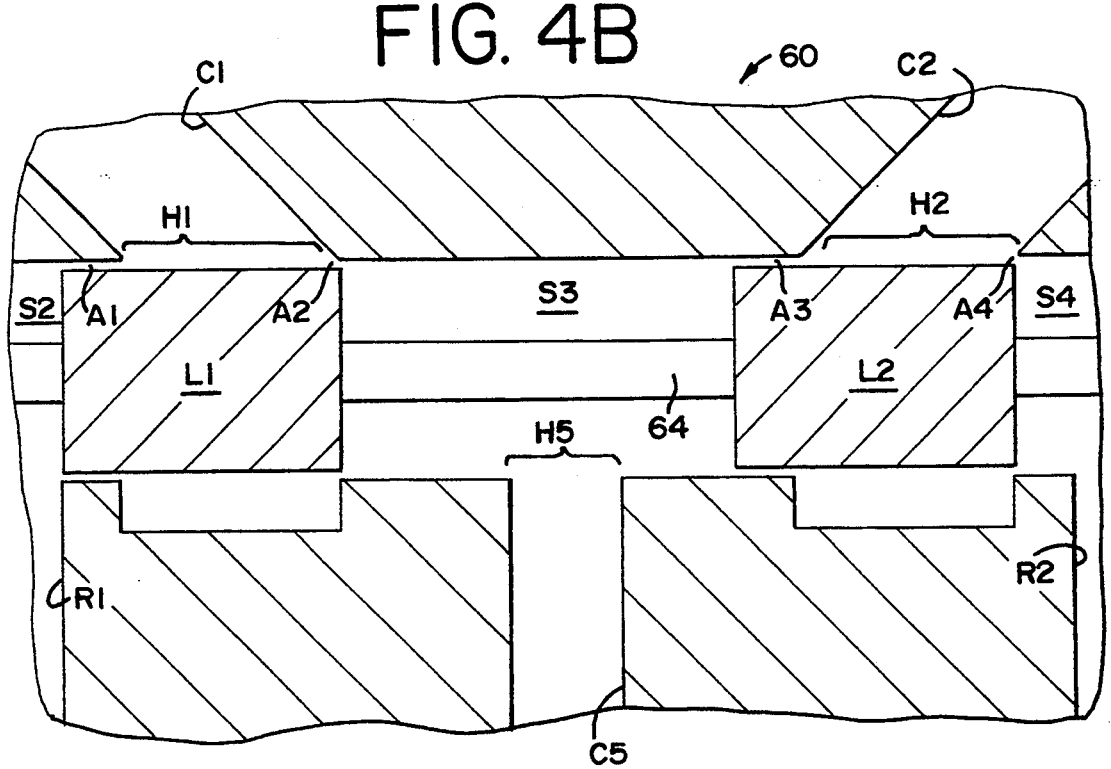

FIG. 4B illustrates the servo valve 60 shifted slightly from the null position toward the left. In this position, there is only a short length of annular clearance A2 at the right-hand end of the valve number L1, and there is a longer length of clearance A1 at the left-hand end of the valve number L1. Thus, there is significantly less pressure drop through the clearance A2 than through the clearance A1, and the pressure drop across the clearance A2 in the moved position illustrated in FIG. 4B is much less than the pressure drop across A2 in the null position illustrated in FIG. 4A. As a result, the pressure in the extension line C1 for the servo valve position illustrated in 4B is higher than it is for the servo valve position illustrated in FIG. 4A. As an example, whereas the pressure in C1 may be one-half the supply pressure when the valve 60 is positioned as in FIG. 4A, the pressure in C1 may be ¾ of the supply pressure when the valve 60 is positioned as shown in FIG. 4B.

The right-hand valve member L2 is shown in FIG. 4B as having moved further to the left compared to the position shown in FIG. 4A. Accordingly, the annular clearance A3 is longer, and the annular clearance A4 is shorter. The pressure drop across the clearance A3 is now greater than it was when the valve was positioned as shown in FIG. 4A, and the pressure drop across A4 is less than it was when the valve was positioned as shown in FIG. 4A. The resulting pressure in the retraction line C2 will now be less than it was when the valve was positioned as in FIG. 4A. For example, the pressure in the retraction line C2 when the valve is positioned as in FIG. 4B could be ¼ of the supply pressure.

When the servo valve 60 is in the position illustrated in FIG. 4B, with the extension line C1 pressure being ¾ of the supply pressure and with the retraction line C2 pressure being ¼ of the supply pressure, the differential pressure across the actuator piston 46 would be ½ of the supply pressure (i.e., ¾ of the supply pressure in the extension chamber 48 minus ¼ of the supply pressure in the retraction chamber 50), and this differential would urge the piston 46 toward the right.

The relative pressures discussed in the examples above are used for illustrative purposes only. It will be appreciated that other pressure relationships could exist depending on the actual pressure drops caused by the internal configuration and component positions.

During operation of the servo valve 60 when the pressure in the extension line C1 is higher than in the retraction line C2, the servo actuator piston 46 moves against the load, and the force on the left-end of the servo valve spool becomes higher than on the right. This causes the servo valve spool to move to the right and recenters the valve members L1 and L2. The surgeon must pull on the operating lever 54 (to the left) with slightly more force as the load increases. This is a load sensing feature that provides tactile feedback to the surgeon.

Conversely, if the surgeon suddenly releases the operating lever 54, then the biasing spring 80 pulls the lever 54 and servo valve spool toward the right. This suddenly causes the retraction line port H2 to close, and the pressure in the retraction line C2 becomes higher than the pressure in the extension line C1. The pressure differential on the ends of the servo valve spool will tend to slow the retraction speed of the actuator 44. Preferably, the restriction orifice 70 (FIGS. 1 and 2) is provided to damp the servo valve spool motion and to prevent the servo actuator 44 from retracting too suddenly if the operating lever input force (F1 in FIG. 3) is released.

ALTERNATE EMBODIMENTS

The output end of the servo actuator piston rod 38 could be connected to a hydraulic piston-cylinder type pump (not illustrated). The servo actuator and hydraulic pump piston areas could be designed with an appropriate area ratio to provide a high pressure hydraulic fluid which would require only low or moderate pressure (gas or liquid) in the servo system. This may be especially useful if it is desired to use a gas such as carbon dioxide or FREON in the servo actuator to provide high pressure hydraulic fluid for portions of the instrument used inside the body cavity.

A mechanical anti-backup mechanism (not illustrated) could be incorporated into the system to prevent the system from locking up prior to the end of the stroke.

FIG. 5 illustrates an alternate spring arrangement for biasing the operating lever to an initial position. In particular, a servo valve 60A is provided with a configuration substantially identical to that described above with reference to the servo valve 60 illustrated in FIGS. 1-4B. However, the tension spring 80 is eliminated and is replaced with a compression spring 80B between the left-hand end of the servo valve cavity and a left-hand end valve member L3A. The servo valve 60A has a valve spool rod 64A to which the valve member L3A, and other valve members (not illustrated), are mounted. The rod 64A is connected to a suitable operating lever (such as the operating lever 54 illustrated in FIG. 1).

FIG. 6 illustrates yet another arrangement for biasing the operating lever to an initial position. An operating lever 54B is connected with a pin 76B to a valve spool rod 64B projecting from a servo valve 60B. The distal end of the rod 64B is biased toward the right with a compression spring 80B which is engaged on one end with the rod 64B and on the other end with a portion 22B of the instrument housing.

As can be seen from the above-described embodiments, the present invention provides amplified actuator forces with low operator input forces. Tactile feedback allows the operator to control the output position and force. The system is particularly suitable for use in stapling and ligating instruments.

It will be readily apparent from the foregoing detailed description of the invention and from the illustrations thereof that numerous variations and modifications may be effected without departing from the true spirit and scope of the novel concepts or principles of this invention.

What is claimed is:

1. A pressurized fluid actuation system suitable for moving an endoscopic or open surgery procedure instrument component, said system comprising:

a double-acting fluid pressure actuator defining an extension chamber and a retraction chamber separated by a piston for engaging said component;

an operating lever pivotally mounted to said piston;

a servo valve that has a valve spool and that is pivotally connected on one end to said lever, said valve being connected to a source of pressurized fluid and having first and second return ports for venting said fluid;

said actuator extension and retraction chambers being connected with said valve for each communicating with said pressurized fluid source and with one of said return ports to control flow in response to the position of said valve spool; and said system including a feedback line communicating between said extension chamber and said valve to apply a force to said valve spool in one direction in response to pressurization of said extension chamber and including a sensing line communicating between said retraction chamber and said valve to apply a force to said valve spool in the opposite direction in response to pressurization of said retraction chamber.

2. The actuation system in accordance with claim 1 in which said valve body defines a cavity for slidably receiving said valve spool and which further defines:

(a) a feedback port connected to said feedback line at a first end of said valve body cavity and a sensing port connected to said sensing line at a second end of said valve body cavity, (b) an extension port and a retraction port between said feedback port and sensing port, said actuator extension chamber being connected with said valve through said extension port, said actuator retraction chamber being connected with said valve through said retraction port, and (c) a supply port between said extension port and said retraction port, said valve being connected to said source of pressurized fluid through said supply port;

said first return port being located between said feedback port and said extension port, said second return port being located between said sensing port and said retraction port; and said valve spool having four longitudinally spaced-apart valve members, one of the two outer valve members being disposed between said feedback port and said first return port, the other of the two outer valve members being disposed between said sensing port and said second return port, said middle two valve members being spaced to 1) increase flow through said extension port to said actuator extension chamber and simultaneously reduce flow through said retraction port when said spool is pulled by said lever toward said cavity first end whereby said piston is extended, and 2) substantially equalize the pressures at said extension and retraction ports when said spool is restrained by said lever in a moved position whereby said piston is held in an extended position.

3. The actuation system in accordance with claim 1 in which said fluid pressure actuator is a hydraulic actuator having a housing.

4. The actuation system in accordance with claim 3 in which said fluid pressure actuator piston includes a piston rod which projects through an end of said housing and which is connected to said instrument component.

5. The actuation system in accordance with claim 3 in which said fluid pressure actuator piston includes a piston rod which projects through an end of said housing and which is pivotally connected to said lever.

6. The actuation system in accordance with claim 3 in which said fluid pressure actuator piston includes two oppositely extending piston rods which each extends through an associated end of said housing, one of said rods being pivotally connected to said lever and the other of said rods being connected to said instrument component.

7. The actuation system in accordance with claim 1 in which said actuation system further includes a biasing means for biasing said valve spool toward one end of said valve body.

8. The actuation system in accordance with claim 1 in which said actuation system further includes a flow restrictor in said sensing line to restrict flow through said sensing port.

9. A pressurized fluid actuation system suitable for moving an endoscopic or open surgery procedure instrument component, said system comprising:
   a double-acting fluid pressure actuator having a housing defining an extension chamber and a retraction chamber separated by a piston slidably disposed in said housing for engaging said component;
   an operating lever pivotally mounted to said piston;
   a valve having a body defining a cavity and having a spool that is slidably disposed in said cavity and that is pivotally connected on one end to said lever, said valve body defining:
   (a) a feedback port at a first end of said valve body cavity and a sensing port at a second end of said valve body cavity,
   (b) an extension port and an retraction port between said feedback port and sensing port,
   (c) a supply port between said extension port and said retraction port for admitting pressurized fluid from a source,
   (d) a first return port between said feedback port and said extension port for venting said fluid, and
   (e) a second return port between said sensing port and said retraction port for venting said fluid;
   a first passage system communicating between said actuator extension chamber, said valve body feedback port, and said valve body extension port;
   a second passage system communicating between said actuator retraction chamber, said valve body sensing port, and said valve body retraction port;
   said valve spool having four longitudinally spaced-apart valve members, one of the two outer valve members being disposed between said feedback port and said first return port, the other of the two outer valve members being disposed between said sensing port and said second return port;
   a biasing means for pivoting said lever to urge said valve spool toward said valve cavity second end; and
   said middle two valve members being spaced to
   1) increase flow through said extension port to said actuator extension chamber and simultaneously reduce flow through said retraction port when said spool is pulled by said lever toward said cavity first end whereby said piston is extended,
   2) substantially equalize the pressures at said extension and retraction ports when said spool is restrained by said lever in a moved position whereby said piston is held in an extended position, and
   3) permit differential leakage across said middle two valve members when said lever is released which results in a pressure at said retraction port that is greater than the pressure at said extension port when said lever is released and said biasing means urges said spool to an intermediate position in said cavity whereby said piston is retracted.

10. The actuation system in accordance with claim 9 in which said fluid pressure actuator is a hydraulic actuator having a generally cylindrical housing.

11. The actuation system in accordance with claim 9 in which said fluid pressure actuator piston includes a piston rod which projects through an end of said housing and which is connected to said instrument component.

12. The actuation system in accordance with claim 9 in which said fluid pressure actuator piston includes a piston rod which projects through an end of said housing and which is pivotally connected to said lever.

13. The actuation system in accordance with claim 9 in which said fluid pressure actuator piston includes two oppositely extending piston rods which each extends through an associated end of said housing, one of said rods being pivotally connected to said lever and the other of said rods being connected to said instrument component.

14. The actuation system in accordance with claim 9 in which said actuation system further includes a flow restrictor in said second passage system to restrict flow through said sensing port.

* * * * *